(12) United States Patent
Hayashi et al.

(10) Patent No.: US 8,476,273 B2
(45) Date of Patent: Jul. 2, 2013

(54) SMALL MOLECULE INHIBITORS OF LCK SH2 DOMAIN BINDING

(75) Inventors: Jun Hayashi, Ellicott City, MD (US); Alexander Mackerell, Baltimore, MD (US); Younus Mia, Ellicott City, MD (US); Guanjun Xia, Baltimore, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 215 days.

(21) Appl. No.: 12/674,685

(22) PCT Filed: Aug. 18, 2008

(86) PCT No.: PCT/US2008/073498
§ 371 (c)(1),
(2), (4) Date: Apr. 13, 2011

(87) PCT Pub. No.: WO2009/026239
PCT Pub. Date: Feb. 26, 2009

(65) Prior Publication Data
US 2011/0183984 A1    Jul. 28, 2011

Related U.S. Application Data

(60) Provisional application No. 60/956,471, filed on Aug. 17, 2007.

(51) Int. Cl.
*A61K 31/501* (2006.01)
*A61K 31/44* (2006.01)
*A61K 31/16* (2006.01)
*A61K 31/15* (2006.01)

(52) U.S. Cl.
USPC ...... 514/252.01; 514/299; 514/345; 514/615; 514/639

(58) Field of Classification Search
USPC .............. 514/252.01, 299, 345, 615, 639
See application file for complete search history.

(56) References Cited

FOREIGN PATENT DOCUMENTS
WO    WO2007002433    1/2007

OTHER PUBLICATIONS

Braselmann et al. "An Orally Available Spleen Tyrosine Kinase Inhibitor Blocks Fc Receptor Signaling and Reduced Immune Complex-Mediated Inflammation." JPET, 2006, vol. 319, pp. 998-1008.
Stachlewitz et al. "A Novel and Selective Small-Molecule Inhibitor of Lck, Prevents Heart Allograft Rejection." JPET, 2005, vol. 315, pp. 36-41.

*Primary Examiner* — Renee Claytor
(74) *Attorney, Agent, or Firm* — Marianne Fuierer; Moore & Van Allen, PLLC (57) ABSTRACT

The present invention provides materials and methods for modulating an immune response. The materials and methods may be used to treat diseases associated with an aberrant immune response. In some embodiments, materials and methods of the invention may be used to treat autoimmune diseases, for example, rheumatoid arthritis.

5 Claims, 7 Drawing Sheets

SMALL MOLECULE INHIBITORS OF LCK SH2 DOMAIN BINDING

CROSS REFERENCE TO RELATED APPLICATIONS

This application claims priority to U.S. provisional application Ser. No. 60/956,471 filed Aug. 17, 2007, the entire contents of which are specifically incorporated herein by reference.

STATEMENT REGARDING FEDERALLY SPONSORED RESEARCH

The invention was made with United States Government support under Contract No. CA095200 from the National Institutes of Health. The United States Government has certain rights in the invention.

BACKGROUND

The role of Lck kinase in T cell activation is well established. The key step in the TCR proximal activation signals mediated by Lck is the phosphorylation of immunoreceptor tyrosine based activation motifs (ITAM) present in the cytoplasmic tails of CD3 chains and the phosphorylation of ZAP-70 kinase. The inhibition of Lck action hampers these initial events preventing the activation of multiple signaling pathways required for IL-2 production and antigen-specific T cell proliferation, thus blocking immune response. Due to its pivotal role in T cell activation and due to its restricted expression, Lck is an attractive molecular target for the development of novel immune response inhibitors.

Lck is a Src family kinase composed of several distinct functional domains, the kinase, SH2 and SH3 domains. Among these functional domains, the kinase and the SH2 domains are attractive targets because of their roles in catalytic action and in defining specificity. Chemical targeting of the Lck kinase domain has been used to achieve a therapeutic outcome. Lck kinase catalytic inhibitors so far developed lack desired specificities and exhibited severe toxicity in vivo making them unsuitable for further drug development. Since similar Src family kinases such as Fyn and Lyn are expressed by lymphoid cells, development of inhibitor compounds that specifically target the Lck kinase is essential. All of the kinase catalytic inhibitors are ATP analogues and lack the desired level of specificity towards other closely related Src family kinases, especially Lyn.

Since SH2 is a functional domain that binds to specific tyrosine phosphorylated sites of proteins, studies have been focused on the relevant portions of the SH2 domain structures, i.e., the region to which the phosphorylated tyrosine (pY) target peptides bind. 3D structural analyses have shown that the binding domain is comprised of a crevice along the surface of the protein to which the phosphopeptide binds in an extended conformation. The crevice includes two well-defined binding pockets for the pY residue and for the pY+3 residue. The binding specificity of SH2 domains are primarily dictated by binding sites that interact with the amino acid residues on the C-terminal side of the pY, especially the third residue (pY+3 sites). Lck has been shown to bind with the highest affinity to the ζ chain ITAM-2 C terminal phosphotyrosine residues. Such selectivity of SH2 domain is essential for a proper cellular activation and suggests that SH2 domains may be potential targets for the design of compounds that specifically inhibit selected signal transduction pathways. Blocking the association of Lck SH2 domain with the CD3 ITAM prevents T cell activation. Accordingly, Lck SH2 domain is a potential target for immunosuppressive drug development.

Based on the vast knowledge of SH2 domain 3D structure and the sequence specificity of SH2 domains, rational design of peptides and peptidomimetics that are specific for individual SH2 domains has been performed. However, these peptidomimetics presented problems of stability and permeability that limited their further development into therapeutic agents. To address this limitation, the discovery of small molecular-weight non-peptidic compounds targeted towards the pY+3 binding pocket that specifically block SH2 domain binding to its cellular target protein has been carried out as an approach for the development of novel immunosuppressants.

SH2 domains have been the target of a large number of 3D structural studies as well as computational studies via molecular simulations. Currently, there are over 220 structures available in the NCBI Protein Data Bank that include SH2 domains alone and in complex with various peptides. Using the available structural information of Lck SH2 domains in the database, computer aided drug design (CADD) was used to identify small molecule inhibitors of Lck SH2 (SMILS) targeting the pY+3 binding pocket. Three compounds were identified to be selective in inhibiting Lck SH2 domain binding to the CD3 ζ chain ITAM. These SMILS inhibited IL-2 production, mixed lymphocyte reaction in vitro and popliteal lymph node assay in vivo.

Rheumatoid arthritis (RA) is a chronic multi-system T cell autoimmune disease. Several lines of evidence derived from research on the rat adjuvant arthritis (AA) experimental model support an etiologic relationship between AA and chronic inflammatory RA in humans. For example: a) in RA patients, an association between T cell responses to mycobacterial hsp65 (Bhsp65) and early stages of joint inflammation has been noted; b) T cell responses to Bhsp65 are elevated in RA synovial fluid compared with blood; c) RA patients raise T cell responses not only to native Bhsp65 but also to its peptide 180-188 (the arthritogenic determinant for AA in the Lewis rat); d) arthritis patients with juvenile chronic arthritis also raise vigorous T cell responses to BhspB5 and self hsp65. Thus, T cell responses to Hsp antigens are involved in the disease process in RA. Among the subsets of T cells, it is believed that Th1 cells are involved in the pathogenesis of T cell autoimmune diseases. Shifting of differentiation of autoreactive T cells towards the Th2 effector phenotype is associated with the improvement of RA.

The predominantly T cell-mediated nature of the disease process, the well-established experimental model of AA in Lewis rat that closely resembles human RA, the well-defined pathogenic epitope within Bhsp65, the well-characterized pathogenic epitope-specific T helper 1 (Th1) subset, and the AA-protective attribute of anti-Bhsp65 antibodies provide unique opportunities for the validation and the analysis of the mechanism of action of SMILS.

Upon antigen-mediated activation, T cell antigen receptor complex becomes phosphorylated at ITAM residues. Although there are numerous signaling proteins with SH2 domains in T cells, only a few bind to the ITAM via their SH2 domains. Thus, in phosphotyrosine based signaling events, the specificity is determined by the SH2 domain. A successful strategy to identify small molecule inhibitory compounds targeting the SH2 domain pY+3 binding pocket using combination of CADD and in vitro solid phase EIA screening methods has been developed. Among the compounds selected in the screening process, compounds have been identified that have restricted specificity, only inhibiting the association of Lck SH2 domain with the CD3 ζ chain ITAM but not the relatives of Lck in the Src family such as Fyn and Lyn. Identification of small molecule inhibitors that can discriminate between such closely related SH2 domains is novel. The striking specificity of these compounds towards Lck SH2 domain, their permeability and low toxicity make them attractive as immunosuppressants.

The present invention provides specific non peptide small molecule inhibitors that block Lck SH2 association with the tyrosine phosphorylated ITAMs of CD3 chains. These compounds (small molecule inhibitors of Lck SH2 domain:S-MILS) specifically inhibit Lck function and block IL-2 production by activated T cells, mixed lymphocyte reaction in vitro as well as local allogeneic response of popliteal lymph node assay in vivo and mycobacteria-induced (Mtb-induced) adjuvant arthritis in rats. Compounds are cell permeable, non-cytotoxic and well tolerated by animals without any visible toxic effects. These compounds specifically suppress T cell activation and reduced joint inflammation in arthritic rats. Immunosuppressors can be used in the treatment of severe rheumatoid arthritis.

SUMMARY OF THE INVENTION

In one embodiment, the invention relates to a method of achieving an immunomodulatory effect in a patient in need thereof, comprising administering an effective amount of one or more of the compounds of the invention. Compounds of the invention include compounds 72, 87, and 241 as described in more detail below. An immunomodulatory effect may be stimulation of an immune response or suppression of an immune response. In one embodiment, compounds of the invention may be administered to a patient in thereof in order to suppress an undesired immune response.

In one embodiment, the present invention provides methods of modulating the activity of Lck kinase in a patient in need thereof. Such methods may comprise administering to the patient an effective amount of a compound selected from the group consisting of compounds 72, 87, and 241. Modulation of Lck kinase activity includes, but is not limited to, inhibiting kinase activity and inhibiting binding of the SH2 domain of Lck kinase to ITAM.

In one embodiment, the present invention provides materials and methods for treating an autoimmune disease in a patient. Such methods may comprise administering to the patient an effective amount of a compound selected from the group consisting of compounds 72, 87, and 241. Any autoimmune disease may be treated using the compounds of the invention. Examples of autoimmune diseases that can be treated using the compounds of the invention include, but are not limited to, rheumatoid arthritis, glomerulonephritis, Hashimoto's thyroiditis, multiple sclerosis, T cell leukemia, systemic lupus erythematosus, myasthenia gravis, autoimmune hemolytic anemia, autoimmune thrombocytopenic purpura, type 1 diabetes, Chrohn's disease, Grave's disease, and celiac disease.

In one embodiment, the present invention provides materials and methods of treating swelling of joints associated with a disease, for example, rheumatoid arthritis. Such methods may comprise administering an effective amount of a compound of the invention, for example, a compound selected from the group consisting of compounds 72, 87, and 241.

In one embodiment, the present invention provides a method of inhibiting the activation of T cells. Such methods may comprise contacting the T cells with a compound selected from the group consisting of compounds 72, 87, and 241. The T cells to be contacted may be in vivo, for example, in a patient or in vitro, for example, may have been removed from a patient and/or may have been grown in culture.

BRIEF DESCRIPTION OF THE DRAWINGS

FIG. 3 is a bar graph showing the results of the Popliteal Lymph Node (PLN) assay. SMILS (1 mg or 0.1 mg/kg body weight) were injected ip. every day from day 0 to day 4 to ICR mice (n=3) that received footpad injections of $1 \times 10^6$ C3H mice lymph node cells (LNC) on day 0. Mice were killed on day 6 and their PLN collected and weighed. Positive control group (P) received footpad injections of LNC and ip. injection of PBS while negative controls (N) received only PBS injections both in the footpad and ip. CsA control received 1 mg/kg body weight cyclosporin A. Error bars represent the mean±SD of six PLN. The experiment was repeated two times. SMILS and CsA treatments significantly inhibited PLN (*$p<0.05$) compared to the positive controls for all doses. No significant differences (†$p>0.05$) were observed between the SMILS (1 mg/kg body weight) and CsA treated and the negative controls.

DETAILED DESCRIPTION

As used herein, treating a disease, means preventing, slowing the onset of, and/or ameliorating the disease and/or at least one sign or symptom of the disease.

The present invention relates to useful forms of the compounds as disclosed herein, such as pharmaceutically acceptable salts and prodrugs of all the compounds of the present invention. Pharmaceutically acceptable salts include those obtained by reacting the main compound, functioning as a base, with an inorganic or organic acid to form a salt, for example, salts of hydrochloric acid, sulfuric acid, phosphoric acid, methane sulfuric acid, camphor sulfonic acid, oxalic acid, maleic acid, succinic acid and citric acid.

Pharmaceutically acceptable salts also include those in which the main compound functions as an acid and is reacted with an appropriate base to form, e.g., sodium, potassium, calcium, magnesium, ammonium, and chlorine salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyannates, tosylates, mesylates and undecanoates.

Preferably, the salts formed are pharmaceutically acceptable for administration to mammals, for example, humans. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

The compounds of the invention can be administered alone or as an ingredient, for example, an active ingredient, in a composition such as a formulation. Thus, the present invention also includes pharmaceutical compositions of a compound of the invention or a salt thereof, containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Isol, editor), 1553-1593 (current edition).

In view of their high degree of selectivity for Lck kinase, the compounds of the present invention can be administered to anyone requiring Lck kinase modulation. Administration may be accomplished according to patient needs, for example, orally, nasally, parenterally (subcutaneously, intravenously, intramuscularly, intrasternally, and by infusion) by inhalation, rectally, vaginally, topically and by ocular administration. Injection can be, e.g., intramuscular, intraperitoneal, intravenous, etc.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time-release capsules, tablets and gels are also advantageous in administering the compounds of the present invention.

Various liquid oral dosage forms can also be used for administering compounds of the inventions, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents, such as other agents which inhibit or stimulate tyrosine kinases, signal transduction processes, cell proliferation and/ or immune responses. Inhibitory agents include, e.g., cyclosporine, FK506, rapamycin, leflunomide, butenamindes, corticosteroids, atomeric acid, dipeptide derivative, tyrphostin, Doxorubicin or the like. In such combinations, each active ingredient can be administered either in accordance with its usual dosage range or a dose below its usual dosage range.

The dosages of the compounds of the present invention depend upon a variety of factors including the particular syndrome to be treated, the severity of the symptoms, the age, sex and physical condition of the patient, the route of administration, the frequency of the dosage interval, the particular compound utilized, the efficacy, toxicology profile, pharmacokinetic profile of the compound, and the presence of any deleterious side-effects, among other considerations.

An "effective amount," in reference to the methods of the invention, for example, methods of modulating of an immune response, is an amount sufficient for preventing, slowing the onset of ameliorating and/or treating any condition, for example, those associated with an aberrant immune response. For example, an effective amount to treat 1) an autoimmune disorder refers to an amount sufficient to bring about one or more of the following results: inhibit or ameliorate one or more of the symptoms of the disease; inhibit progressive degeneration of cells involved in the disorder; relieve discomfort due to the disorder; and prolong the life of a patient suffering from the disorder; 2) a patient undergoing tissue or organ transplantation refers to an amount sufficient to bring about one or more of the following results: inhibit or prevent rejection of the transplanted material; relieve discomfort resulting from rejection of the transplant; and prolong the life of a patient receiving a transplant; 3) an immunosuppressive patient refers to an amount sufficient to bring about one or more of the following results: increase the number of T cells or number of activated T cells; reduce the immunosuppressed state of the patient; relieve discomfort due to the disorder; and prolong the life of a patient suffering from the disorder.

The compounds of the invention are administered at dosage levels and in a manner customary for Lck kinase inhibitors or stimulators, or other analogous drugs, such as those mentioned above. For example, cyclosporine is administered (for transplants) at about 7.95±2.81 mg/kg/day (see PDR (Physician's Desk Reference)); FK506 is administered (for transplants) at about 0.15-0.30 mg/kg/day (see PDR); and rapamycin is administered (for transplants) at about 2-6 mg/day, e.g., about 0.024 mg/kg/day for an 81 kg adult (see Thomas A. Stargy Transplantation Institute web site). See also, e.g., disclosures in U.S. Pat. Nos. 5,688,824, 5,914,343, 5,217,999, 6,133,301 and publications cited therein.

For example, compounds of the invention or a salt thereof, can be administered, in single or multiple doses, at a dosage level of, for example, 1 µg/kg to 500 mg/kg of body weight of patient/day, preferably between about 100 µg/kg/day and 25 mg/kg/day. Dosages can be adjusted so as to generate an immunomodulatory effect, as desired. A lower dosage can be between about 1 µg/kg/day and 750 µg/kg/day, preferably between about 10 µg/kg/day and 500 mg/kg/day. A higher dosage can be between about 1 mg/kg/day and 750 mg/kg/day, preferably between about 10 mg/kg/day and 450 mg/kg/day.

Methods of Use

The compositions of the invention can be used for preventing, slowing the onset of, ameliorating and/or treating any disease associated with an aberrant immune response.

In one embodiment, the present invention includes methods of treating patients suffering from depressed immune systems resulting from, e.g., chemotherapy treatment, radiation treatment, radiation sickness, or HIV/AIDS; conditions associated with primary B-cell deficiency (such as, e.g., Bruton's congenital a-γ-globulinemia or common variable immunodeficiency) or primary T-cell deficiency (such as, e.g., the DiGeorge and Nezelof syndromes, ataxia telangiectasia or Wiskott-Aldrich syndrome); severe combined immunodeficiency (SCID), etc. with a compound of the invention. The compounds can also be used in conjunction with vaccines (e.g., anti-bacterial, anti-fungal, anti-viral or anti-protozoiasis), particularly for patients having immunocompromised states.

In another preferred embodiment, the invention includes methods of treating patients suffering from autoimmune disorders, such as, e.g., rheumatoid arthritis, glomerulonephritis, Hashimoto's thyroiditis, multiple sclerosis, T cell leukemia, systemic lupus erythematosus, myasthenia gravis, autoimmune hemolytic anemia, autoimmune thrombocytopenic purpura, type 1 diabetes, Chrohn's disease, Grave's disease, celiac disease, or the like, with a compound of the invention. Compounds of the invention are also useful for treating tissue or organ transplant rejection, e.g., hyper-acute or chronic graft-vs-host disease, allograft or xenograft rejection, etc.

In some embodiments, compositions of the invention may be given repeatedly over a protracted period, i.e., may be chronically administered. Typically, compositions may be administered one or more times each day in an amount suitable to prevent, reduce the likelihood of an attack of, or reduce the severity of an attack of the underlying disease condition. Such compositions may be administered chronically, for example, one or more times daily over a plurality of days.

In some embodiments, compositions of the invention may be use to treat acute attacks of the underlying disease. Typically, embodiments of this type will require administration of the compositions of the invention to a subject undergoing an attack in an amount suitable to reduce the severity of the attack. One or more administration may be used.

The following examples are provided for illustrative purposes only, and are in no way intended to limit the scope of the present invention.

EXAMPLE 1

Identification of SMILS that Blocks Lck SH2 Domain Association with the CD3 ζ Chain pY-ITAM Compounds have been identified that inhibited Lck SH2 domain binding to the CD3 ζ chain ITAM peptide using a combination of CADD and biological assays using a solid phase EIA assay developed in our laboratory. Using this screening 42 out of 190 test compounds inhibited the ITAM binding of Lck SH2 domains by more than 60% at 100 µM concentration (data not shown).

Lck kinase is a member of Src family kinases including Fyn, Lyn, and Hck that have SH2 domains sharing significant sequence homologies at βD5, βE4, EF1 and βG4 sites where these amino acids form the pY+3 binding pocket. Accordingly, it was important to test inhibition specificities of compounds against SH2 domains of these Src kinases and other signal transduction molecules involved in TCR proximal signaling. All 42 compounds identified in the above assay were subjected to specificity screening using a solid phase EIA assay using 7 different GST-SH2 domains (Lck, Fyn, Lyn, Hck, Src, She and Grb2). Three compounds, compounds 72, 87 and 241 showed specificities towards Lck SH2 domain while displaying little or no inhibitory activity against the other SH2 domains at a screening concentration of 100 µM.

The structures of these compounds are provided below

The solid phase specificity screening that was used allowed selection of compounds that selectively inhibited Lck kinase SH2 domain binding. All the compounds that had >40% inhibitory effect in the cellular assays were tested in the solid phase specificity screening assay and three compounds, 72, 87 and 241 were identified to be specific to Lck. Due to the fact that these compounds were specific to Lck SH2 domain, in vitro and in vivo assays described below were conducted using these 3 compounds.

EXAMPLE 2

Inhibition of Mixed Lymphocyte Reaction

Figure 1:
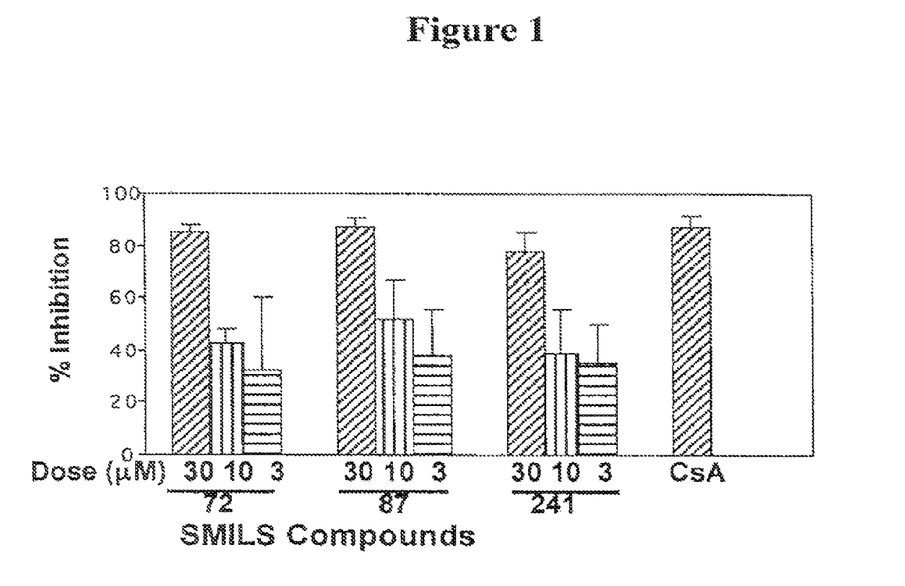
FIG. 1 is a bar graph showing the dose-dependent inhibition of MLR with compounds of the invention. Different concentrations of the compounds were added at 0 h, 24 h and 48 h to the culture of CD-1 and C3H mouse LNC ($5 \times 10^5$ cells from each strain) and $^3$[H]-thymidine (1 mCi/well) was added for the last 18 h of the 72 h culture. The cells were harvested and radioactivity was counted on a Liquid Scintillation Counter. The cells cultured in the absence of the compound (vehicle only) served as the positive control. Equal number of non-allogeneic cells served as the negative control, CsA (1 µM) was used as an additional control. The results were expressed as percent inhibition.

The identified 3 specific SMILS were first tested for their ability to inhibit mixed lymphocyte reaction (MLR), a common assay to assess allogeneic responses of T cells in vitro. Lymph node lymphocyte single cell suspensions from C3H and CD-1 mice ($5 \times 10^5$ cells from each strain) were cultured for 72 h in 200 μl of culture medium in the presence or absence of the test compounds. As shown in FIG. 1, T cell proliferation in response to allogeneic stimulation was inhibited in a dose-dependent manner by the compounds. At 30 μM, the rate of inhibition was equivalent to 1 μM cyclosporin A (CsA). Compounds inhibited MLR using lymphocytes from Lewis and Wister rats equally well.

EXAMPLE 3

Cytotoxicity Test

Figure 2:
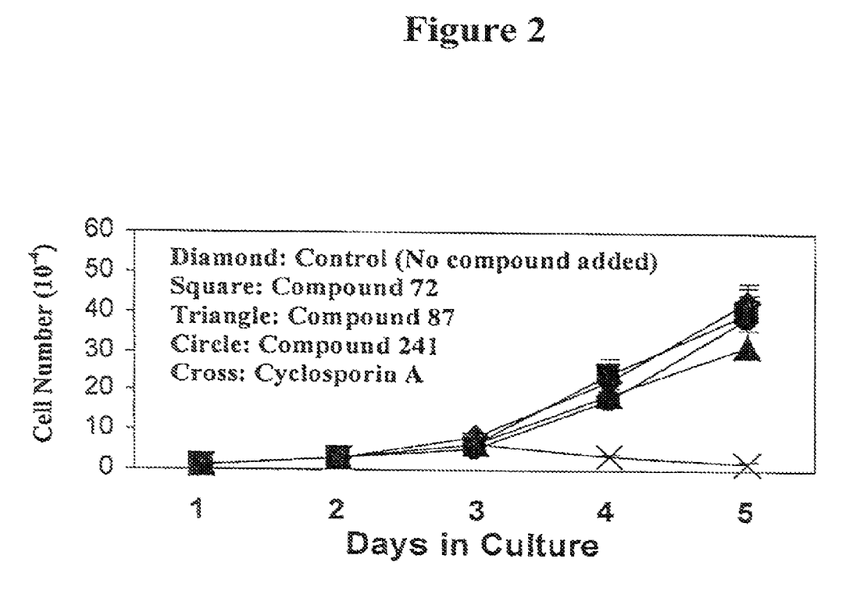
FIG. 2 is a line graph showing the results of the cytotoxicity assay. SMILS compounds (10 µM) were added on days 2, 3, and 4 to Jurkat cells cultured in a 48-well plate ($1 \times 10^4$ cells/well on day 0) in RPMI 1648+10% FBS. Number of cells in each well was counted every day. Error bars represent mean±SD (n=3). Cyclosporin A was used as a control at a dose of 1 µM. No significant differences ($p>0.1$) in the cell number in any day was found between the control and experimental groups except for compound 87 at day 5.

None of the compounds tested showed any cytotoxicity in Jurkat cell growth assay. Compounds 72 and 241 had no effect on cell growth whereas 87 appears to have had a slight cytostatic effect. In contrast, the addition of 1 μM CsA to the culture completely killed Jurkat cells (FIG. 2). Moreover in the MLR assays, the viability of the cells that received compound was similar to that of control cultures. These results indicate that the selected compounds did not have cytotoxic effects in vitro.

EXAMPLE 4

Inhibition of Popliteal Lymph Node Local Allogeneic Response

In order to test the ability of these compounds to block T cell activation in vivo, popliteal lymph node (PLN) assay was carried out. PLN assay enables quantification of a local allogeneic response mounted against allogeneic splenocytes injected to the footpads of mice. Three lead compounds at two concentrations (1 mg/kg and 0.1 mg/kg body weight) were injected i.p. on days 0, 1, 2, 3, and 4. PLNs were harvested on day 7 and weighed.

Figure 3:
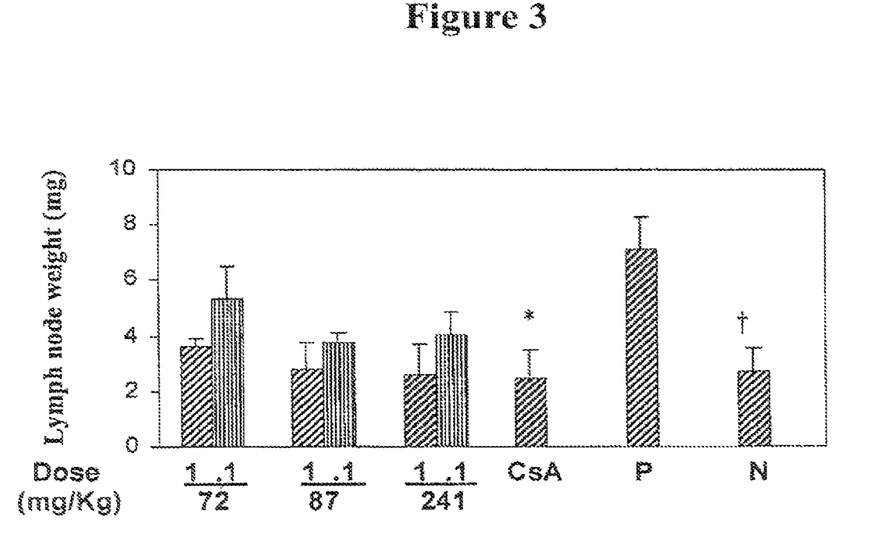

All of the test compounds inhibited allogeneic response of PLN in a dose-dependent fashion (FIG. 3). CsA (1 mg/kg body weight) was used as a positive control. At 1 mg/kg dose, test compounds as well as CsA inhibited PLN to the levels of the negative control (no statistical differences with the negative controls). At 3 mg/kg body weight, CsA was lethal. In contrast, animals receiving test compounds appeared to tolerate compounds well and did not show any side effects such as reduced mobility/activity, diarrhea, weight loss and roughening of fur

EXAMPLE 5

Inhibition of MtB-Induced RA in Rats by SMILS

The predominantly T cell-mediated nature of the disease process, the well-established experimental model of AA in Lewis rat that closely resembles human RA, the well-defined pathogenic epitope within Bhsp65, the well-characterized pathogenic epitope-specific T helper 1 (Th1) subset, and the AA-protective attribute of anti-Bhsp65 antibodies provide unique opportunities for the validation and the analysis of the mechanism of action of SMILS.

Figure 4A:
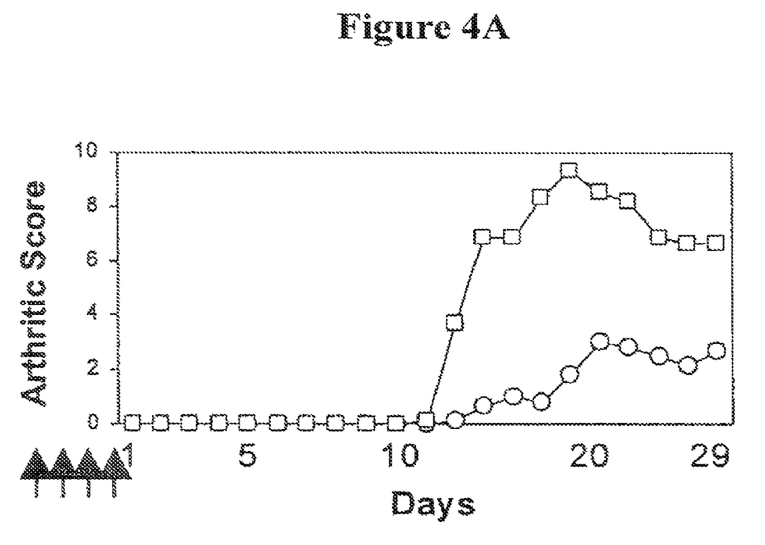
FIG. 4A is a line graph showing the effect of SMILS in a preventive treatment regimen. SMILS injection (indicated by arrows on days −3, −2, −1, and 0) delayed the onset and markedly reduced joint swellings in Mtb-induced AA. Mtb was injected on day 0. □—Untreated group, ○—SMILS treated group.
Figure 4B:
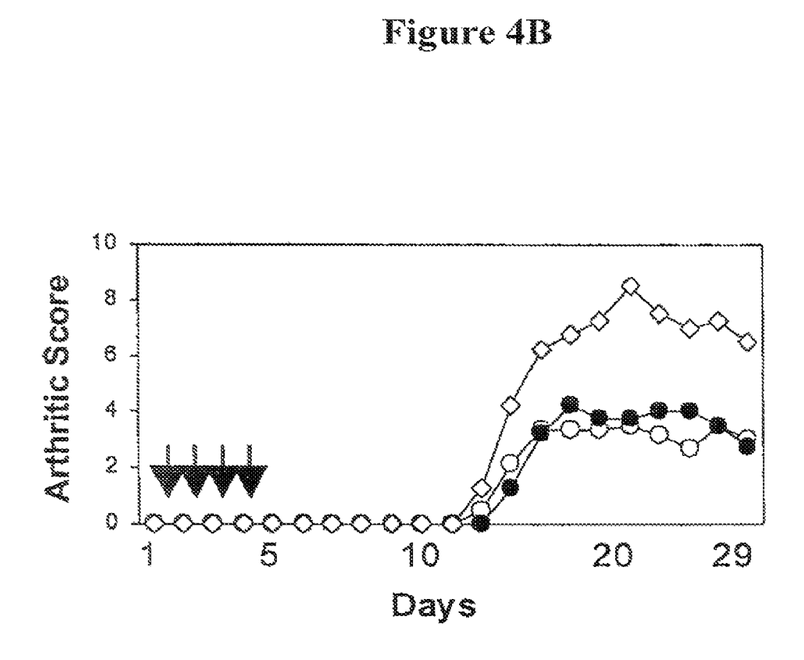
FIG. 4B is a line graph showing the effect of SMILS in therapeutic-1 treatment regimen. SMILS injection (indicated by arrows on days 0, 1, 2, 3, 4) markedly reduced joint swelling in Mtb induced AA. Mtb was injected on day 0. ◇—Untreated group, ○—SMILS treated group (3 mg/kg body weight), ●—SMILS (1 mg/kg body weight) treatment group.
Figure 4C:
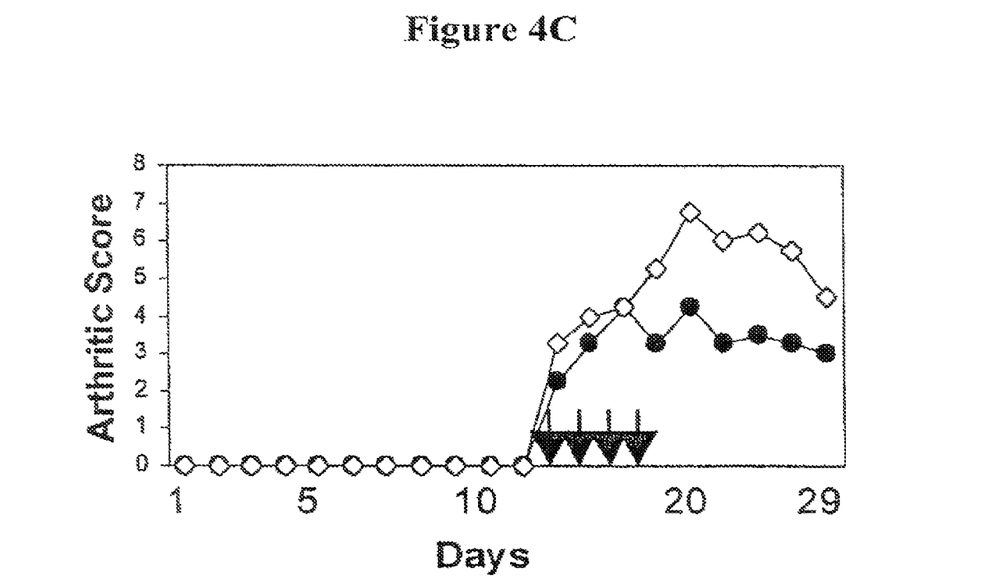
FIG. 4C is a line graph showing the effects of SMILS in therapeutic-2 treatment regimen. SMILS injection (indicated by arrows on days 12, 13, 14, and 15) markedly reduced joint swelling in Mtb induced AA. Mtb was injected on day 0. ◇—Untreated group, ●—SMILS (3 mg/kg body weight) treatment group.
Figure 5A:
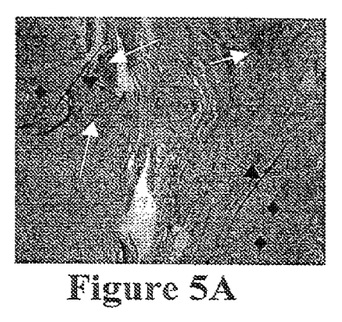
FIG. 5A is a photomicrograph of the hind paw joint of an untreated control rat. Joint cavity indicated between two arrows is filled with inflammatory cells (white arrow). Note that most of the cartilage is eroded and the destruction of the bone by pannus formation (♦).
Figure 5B:
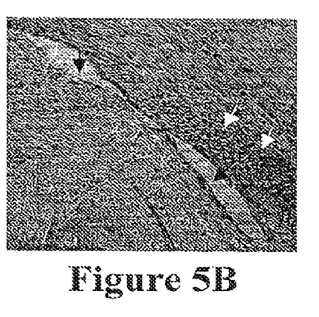
FIG. 5B is a photomicrograph of an untreated rat. Cartilage is totally eroded and the destruction of the bone is evident. Narrowing of joint space is due to the thickening of the synovial membrane (black arrows) and the infiltration of inflammatory cells (white arrows).
Figure 5C:
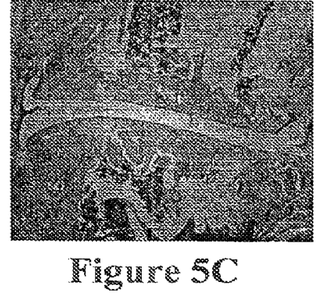
FIG. 5C is a photomicrograph of a compound 241 treated rat. Note the absence of damage to the cartilage and inflammatory cells.
Figure 5D:
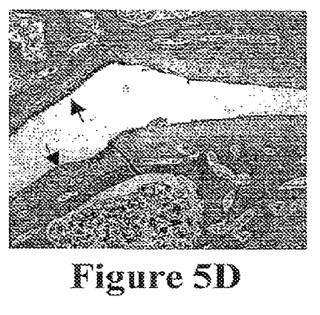
FIG. 5D is a photomicrograph of a compound 241 treated rat. Note thickening of the synovial membrane is some parts of the cartilage (arrows) while other regions remain intact. No infiltration of inflammatory cells is observed in the joint space.

Pilot experiments using Lewis rats were carried out to assess the effect of SMILS on Mtb-induced AA. The initial experiments described here were carried out using compound 241. Experiments were carried out to test the efficacy of SMILS (3 mg/kg body weight injected i.p.) in three treatment regimens: i.e., preventive: (SMILS injected at −3, −2, −1, 0 days before Mtb injection); therapeutic 1: at the time of AA induction (SMILS injected at 0, 1, 2, 3, 4 days after Mtb injection); and therapeutic 2: at the time of clinical symptom appearance (SMILS injected at 10, 11, 12, 13 days after Mtb injection). As shown in FIG. 4A, the preventive regimen delayed the onset of joint swelling and reduced the severity of joint swellings. SMILS was also effective in both therapeutic 1 and 2 treatment regimens and significantly reduced the joint swellings in all rats (FIGS. 4, B and C).

In addition to the visual scoring of the joint swelling, histological examinations of joints from all 4 paws collected at the peak of the disease were carried out. As shown in FIGS. 5 A and B, synovial membrane thickening, erosion of cartilage, destruction of bones by pannus formation, and the infiltration of inflammatory cells into the joint space is observed in the joints of all untreated AA rats, whereas the inflammatory cells were absent from the joint cavity and a limited thickening of synovial membrane only in some joints were observed in SMILS treated rats (FIGS. 5 C and D).

These results clearly show the therapeutic efficacy of SMILS in Mtb-induced AA and indicate the therapeutic potential for rheumatoid arthritis in humans.

Example 6

Effect of SMILS on Vital Organs

Organs (liver, kidney, spleen, lymph node and heart) were also collected from rats treated with 3 mg/kg body weight of SMILS when the experiments described above were terminated. Organs were fixed, embedded and paraffin sections were prepared and stained with hematoxylin and eosin. No differences in cellularity and tissue architectures were observed between control and SMILS treated AA rats (data not shown). Since these organs were isolated from rats at the peak of AA symptoms at different days after SMILS were injected (16, 12 and 3 days in preventive, therapeutic 1 and therapeutic 2 treatment regimens, respectively), an additional experiment was carried out to examine SMILS effect on these organs immediately after 5 consecutive i.p. injections in mice (3 and 30 mg/kg body weight) and vehicle control (0.01% DMSO in PBS).

As in the cases with rats, mice tolerated SMILS treatments well and no visible signs of animals suffering from the treatment (i.e., morbidity, loss of weight, diarrhea, roughening of fur, etc) were observed. Vital organs described above were removed for histological examinations. No significant differences in cellularity and tissue architectures were observed between vehicle control and SMILS treated mice at either the 3 mg or 30 mg/kg body weight dose (data not shown).

Three SMILS compounds that show specificities towards inhibiting Lck SH2 domain association with the CD3 ζ chain ITAM peptide have been identified. These SMILS blocked MLR in vitro and popliteal lymph node assays in vivo and did not appear to have any detectable toxicity both in vitro and in vivo. Finally, SMILS showed therapeutic efficacies in the animal model for RA, the AA in rat. These results conclusively indicate that SMILS inhibit T cell activation both in vitro and in vivo and block RA even after the onset of the clinical symptoms.

While the invention has been described in detail, and with reference to specific embodiments thereof, it will be apparent to one of ordinary skill in the art that various changes and modifications can be made therein without departing from the spirit and scope thereof and such changes and modifications may be practiced within the scope of the appended claims. All patents and publications herein are incorporated by reference to the same extent as if each individual publication was specifically and individually indicated to be incorporated by reference in their entirety.

What is claimed is:

1. A method of modulating the activity of Lck kinase in a patient in need thereof, comprising: administering to the patient an effective amount of a compound selected from the group consisting of compounds 2. The method according to claim 1, wherein the modulation comprises inhibition of binding to ITAM.

3. The method according to claim 1, wherein the modulation comprises inhibiting kinase activity.

4. The method according to claim 1, wherein the effective amount is from about 0.01 mg/kg to 10 mg/kg body weight of the patient.

5. The method according to claim 2, wherein inhibition of binding to ITAM reduces T-cell activation and immune response to provide a treatment for rheumatoid arthritis.

* * * * *

UNITED STATES PATENT AND TRADEMARK OFFICE
CERTIFICATE OF CORRECTION

PATENT NO. : 8,476,273 B2
APPLICATION NO. : 12/674685
DATED : July 2, 2013
INVENTOR(S) : Jun Hayashi et al.

Page 1 of 1

It is certified that error appears in the above-identified patent and that said Letters Patent is hereby corrected as shown below:

In the Specification

Column 1, lines 15-18: "This invention was made with United States Government support under Contract No. CA095200 from the National Institutes of Health. The United States Government has certain rights in this invention."

Should be: "This invention was made with government support under Grant Number CA095200 awarded by the National Institutes of Health. The government has certain rights in the invention."

Signed and Sealed this
Twenty-ninth Day of October, 2013

Teresa Stanek Rea
*Deputy Director of the United States Patent and Trademark Office*